(12) United States Patent
Bowman et al.

(10) Patent No.: US 8,695,850 B2
(45) Date of Patent: Apr. 15, 2014

(54) TIP ARRANGEMENT FOR A DROPPER BOTTLE

(75) Inventors: Lyle Bowman, Pleasanton, CA (US); Surendra Patel, Sunnyvale, CA (US)

(73) Assignee: Insite Vision Incorporated, Alameda, CA (US)

( * ) Notice: Subject to any disclaimer, the term of this patent is extended or adjusted under 35 U.S.C. 154(b) by 962 days.

(21) Appl. No.: 12/399,596

(22) Filed: Mar. 6, 2009

(65) Prior Publication Data

US 2010/0224657 A1    Sep. 9, 2010

(51) Int. Cl.
*B67D 1/00* (2006.01)
*B65D 47/18* (2006.01)

(52) U.S. Cl.
USPC ............................ 222/83; 222/90; 222/420

(58) Field of Classification Search
USPC .................. 222/420, 421, 83, 80, 90, 91
See application file for complete search history.

(56) References Cited

U.S. PATENT DOCUMENTS

| | | | |
|---|---|---|---|
| 4,724,981 A | 2/1988 | Realmuto | |
| 5,246,145 A | 9/1993 | Leoncavallo et al. | |
| 5,261,572 A | 11/1993 | Strater | |
| 5,462,200 A * | 10/1995 | Weiler | 222/83 |
| 5,664,704 A | 9/1997 | Meadows et al. | |
| 5,711,453 A * | 1/1998 | Weiler | 222/83 |
| 5,954,233 A * | 9/1999 | Kawashima et al. | 222/83 |
| 6,076,704 A * | 6/2000 | Weiler et al. | 222/83 |
| 6,247,616 B1 * | 6/2001 | Weiler et al. | 222/83 |
| 6,632,202 B1 | 10/2003 | Hagele | |
| 7,905,369 B2 * | 3/2011 | Hansen | 220/284 |
| 2003/0209570 A1 * | 11/2003 | Joshi et al. | 222/420 |
| 2008/0019863 A1 * | 1/2008 | Kis et al. | 422/20 |

FOREIGN PATENT DOCUMENTS

| | | | | |
|---|---|---|---|---|
| DE | 29613875 U1 | 12/1996 | | |
| EP | 0 425 025 A1 | 5/1991 | | |
| FR | 2622795 | * 11/1987 | | 222/420 |
| WO | WO 2006/058011 A1 | 6/2006 | | |
| WO | WO-2010/084393 A1 | 7/2010 | | |

OTHER PUBLICATIONS

European Office Action issued in European Patent Application No. 10749390.0 mailed on Feb. 5, 2013.
European Search Report issued in European Patent Application No. 10749390.0 dated Jun. 19, 2012.

* cited by examiner

*Primary Examiner* — Kevin P Shaver
*Assistant Examiner* — Stephanie E Williams
(74) *Attorney, Agent, or Firm* — McDermott Will & Emery LLP

(57) ABSTRACT

A tip arrangement for a bottle used for dispensing viscous liquid, such as drops of medicine, is provided. Embodiments include a tip insert having an insert body and a piercing point at a lower end of the insert body, for piercing a top surface of the bottle and for retaining the tip insert on the top surface of the bottle after piercing. A passage extends from a distal end of the piercing point, through the insert body, to an opposing upper surface of the insert body. A dispensing tip at the insert body upper surface communicates with the passage for precisely forming drops of the liquid from the bottle.

11 Claims, 9 Drawing Sheets

TIP ARRANGEMENT FOR A DROPPER BOTTLE

TECHNICAL FIELD

The present disclosure relates to a tip arrangement for a bottle. The present disclosure has particular applicability to bottles used for dispensing drops, such as drops of medicine.

BACKGROUND

Certain conventional dropper bottles are made from a relatively soft plastic resin; filled with a liquid, such as an eye medicine; and shipped from the factory with the top of the bottle sealed to preserve the liquid until it is to be dispensed from the bottle. As shown in FIGS. 7a-c, the top of such a bottle is pierced by the user when the bottle is to be used for the first time. Referring now to FIG. 7a, the bottle is shipped with a piercing cap 71 partially screwed in place, and the top 70 of the bottle unpierced. The cap 71 is then screwed down onto the bottle top 70 by the user, and a spike 71a integrally formed with the cap 71 pierces the top 70 of the bottle (see FIG. 7b). The user then unscrews the cap 71 completely, leaving the pierced top 70 of the bottle exposed, and the bottle ready to dispense drops of the liquid.

While the piercing cap arrangement of FIGS. 7a-c may be adequate for liquids of a certain viscosity range, relatively viscous liquids require a dropper bottle tip having a precise size and shape, which is difficult or impossible to produce from a spike piercing the top of a bottle. As a result, such liquids cannot be successfully dispensed from the conventional bottle and cap arrangement shown in FIGS. 7a-c.

SUMMARY OF THE DISCLOSURE

An advantage of the present disclosure is a tip arrangement for a dropper bottle that enables precise dispensing of high-viscosity liquids from sealed bottles that can be pierced and unsealed when ready to be used for the first time.

According to the present disclosure, the foregoing and other advantages are achieved in part by a tip insert for a dropper bottle containing a fluid. The tip insert comprises an insert body; a piercing point at a lower end of the insert body for piercing a top surface of the bottle and for retaining the tip insert on the top surface of the bottle after piercing; a passage extending from a distal end of the piercing point, through the insert body, to an opposing upper surface of the insert body; and a dispensing tip at the insert body upper surface communicating with the passage for forming drops of the liquid from the bottle.

A further advantage of the present disclosure is a dropper bottle assembly comprising a dropper bottle, a tip insert, and an overcap. The dropper bottle is for containing and dispensing a liquid, and has a top surface, an outer wall adjacent to the top surface, and a first set of threads. The tip insert comprises an insert body; a piercing point at a lower end of the insert body for piercing the top surface of the bottle and for retaining the tip insert on the top surface of the bottle after piercing; a passage extending from a distal end of the piercing point, through the insert body, to an opposing upper surface of the insert body; and a dispensing tip at the insert body upper surface communicating with the passage for forming drops of the liquid from the bottle. The overcap has a second set of threads for engaging the first set of threads to draw the overcap down towards the bottle, and an inner surface for mating with the insert body to guide the piercing point to a predetermined position on the top surface of the bottle prior to piercing the top surface of the bottle. When the first and second sets of threads are engaged to draw the overcap down towards the bottle, the piercing point of the tip insert pierces the top surface of the bottle.

Another advantage of the present disclosure is a method comprising providing a dropper bottle for containing and dispensing a liquid, the bottle having a top surface and a first set of threads; providing a tip insert comprising an insert body, a piercing point at a lower end of the insert body for piercing the top surface of the bottle and for retaining the tip insert on the top surface of the bottle after piercing, a passage extending from a distal end of the piercing point through the insert body to an opposing upper surface of the insert body, and a dispensing tip at the insert body upper surface communicating with the passage for forming drops of the liquid from the bottle; locating the tip insert relative to the bottle such that the piercing point is aligned with the top surface of the bottle; and forcing the piercing point through the top surface of the bottle.

Additional advantages and other features of the present disclosure will be set forth in part in the description which follows and in part will become apparent to those having ordinary skill in the art upon examination of the following or may be learned from the practice of the disclosure. The advantages of the disclosure may be realized and obtained as particularly pointed out in the appended claims.

As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

BRIEF DESCRIPTION OF THE DRAWINGS

Reference is made to the attached drawings, wherein elements having the same reference numeral designations represent like elements throughout, and wherein.

DETAILED DESCRIPTION

The present disclosure addresses and solves the problem of providing high-viscosity liquids, such as certain medicines, in sealed bottles that can be pierced and unsealed when ready to be used for the first time. The present disclosure advantageously provides a tip arrangement for a dropper bottle including a tip insert having a sharp point at its lower end for piercing the top of the bottle, a passage extending from the sharp lower point to an opposing upper surface of the tip insert, and a precisely formed dispensing tip in the upper surface communicating with the passage. The sharp lower point of the tip insert is forced through the top of the bottle to pierce it; for example, by an overcap which screws onto the bottle and fits over the tip insert. After piercing the bottle, the dispensing tip at the upper surface of the tip insert provides the proper size orifice to dispense the liquid inside the bottle.

Figure 1:
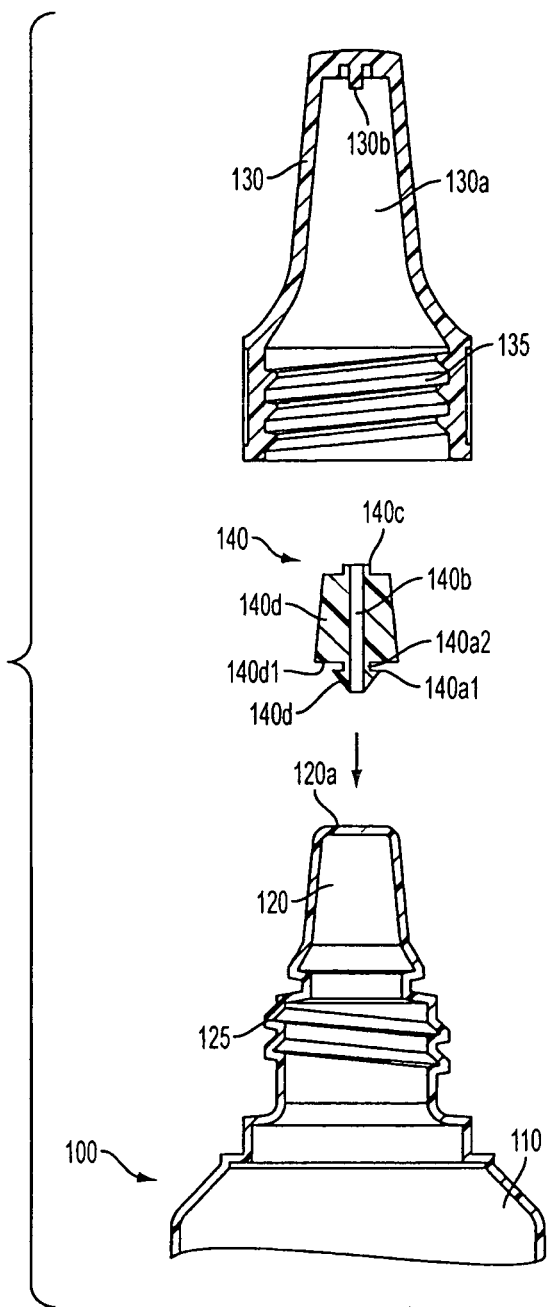
FIGS. 1-3 are cross-sectional views of a tip arrangement for a bottle according to a first embodiment of the present disclosure.

A first embodiment of a tip arrangement according to the present disclosure will now be described with reference to FIGS. 1-3. A bottle 100 comprises a flexible plastic resin reservoir portion 110 and a plastic top portion 120 having threads. 125 and a flat top surface 120a. An overcap 130 having threads 135 to mate with the threads 125 of bottle 100 has an inner cavity 130a which mates with the outer walls of top portion 120 of bottle 100. A tip insert 140 mates with cavity 130a, and has an insert body 140d, a sharp piercing point 140a at a lower end of insert body 140d for piercing the top surface 120a of the bottle 100, a passage 140b extending from the distal end of the sharp piercing point 140a, through insert body 140d, to an opposing upper surface of the insert body 140d, and a precisely formed dispensing tip 140c in the upper body surface communicating with the passage 140b. Dispensing tip 140c has a surface area (i.e., a width and a height) such that it forms small drops of the high-viscosity liquid to be dispensed from bottle 100.

After the piercing point 140a pierces the top surface 120a of the bottle 100, it retains the tip insert 140 on the top surface 120a of bottle 100. The piercing point 140a includes a flange 140a1 substantially parallel to the tip insert body lower surface 140d1, and a shaft 140a2 disposed between the flange 140a1 and the tip insert body lower surface 140d1. The shaft 140a2 has a length substantially the same as a thickness of the bottle top surface 120a. The bottle top surface 120a is captured between the flange 140a1 and the tip insert body lower surface 140d1 after piercing by the piercing point 140d to retain the tip insert 140 on the top surface 120a.

Figure 2:
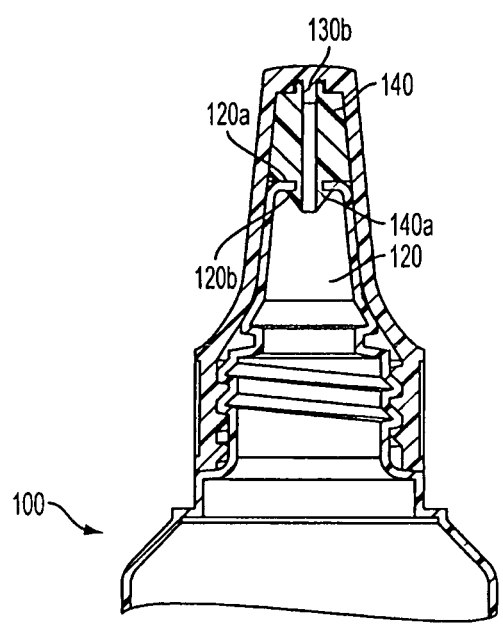
Figure 3:
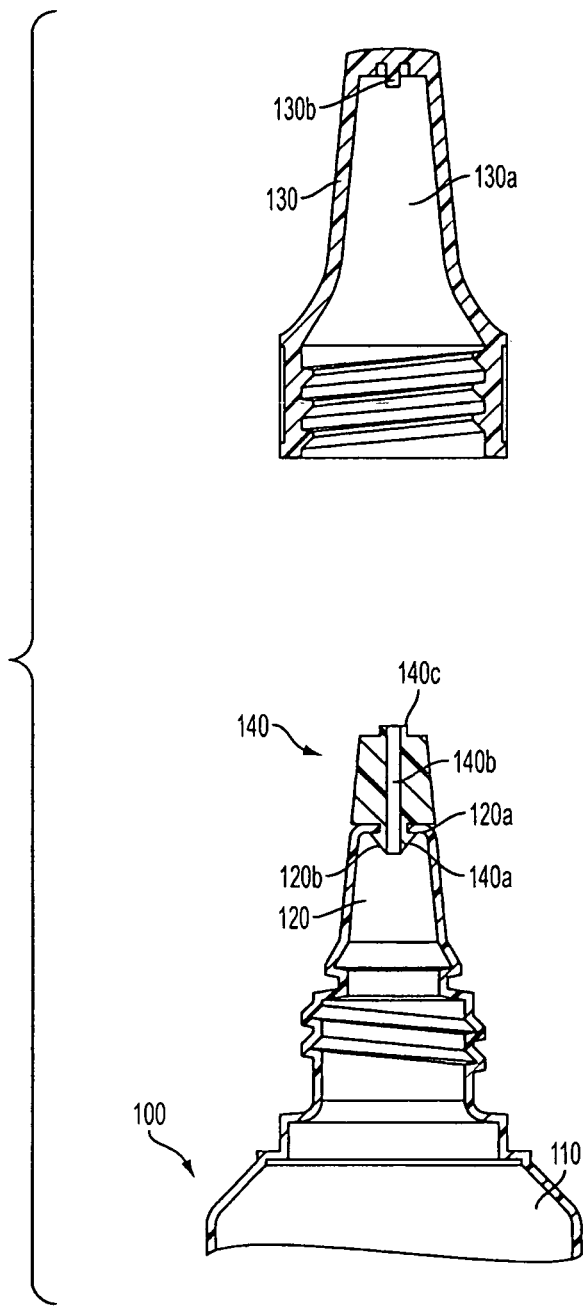

In use, the tip insert 140 is inserted into the overcap cavity 130a as shown in FIG. 2, such that an extension 130b of overcap 130 engages the dispensing tip 140c. The overcap 130 is then threaded onto bottle 100, thereby locating and aligning the piercing point 140a of tip insert 140 with the top surface 120a of the bottle 100 at a predetermined position. The engaging sets of threads 125, 135 draw the overcap 130 down towards the bottle 100 until the piercing point 140a of the tip insert 140 is forced through the top 120a of the bottle, to pierce it. After piercing the bottle top 120a, and unscrewing the threads to remove the overcap 130, the dispensing tip 140c provides the proper size orifice to dispense a liquid inside the bottle (see FIG. 3). Moreover, after the bottle top 120a is pierced, and the overcap 130 is threaded back onto the bottle 100 completely, the extension 130b engages the orifice of the dispensing tip 140c to prevent leakage of the liquid.

Figure 4:
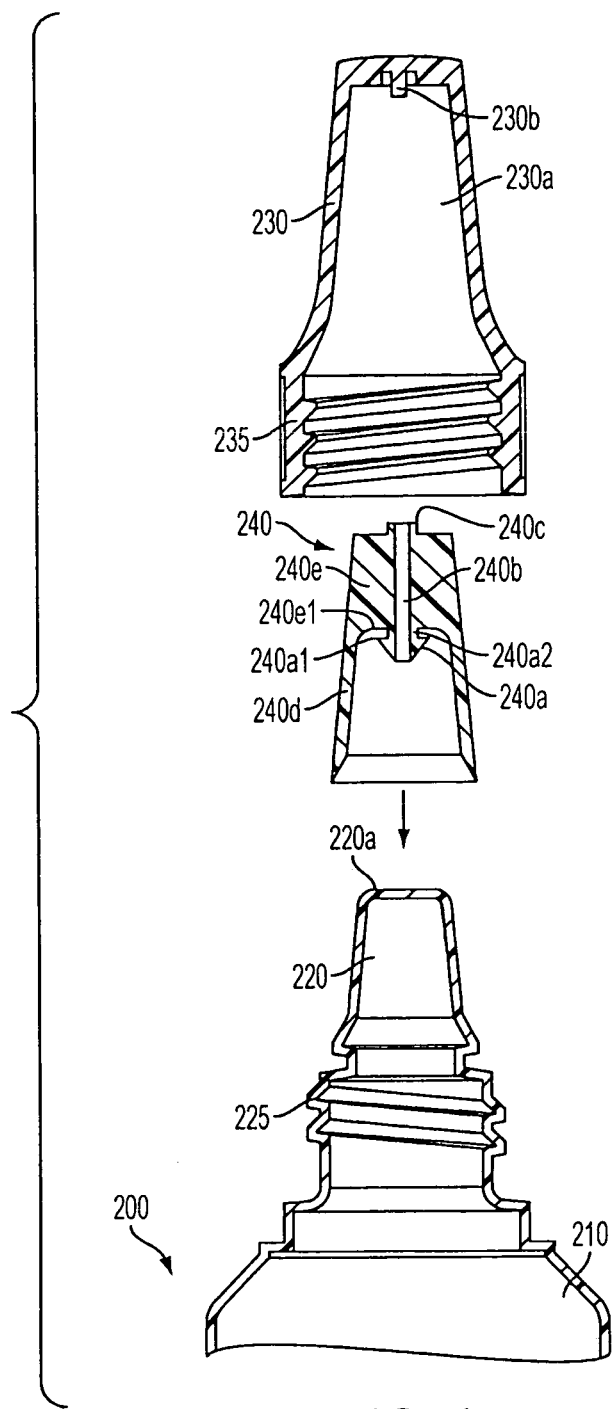
FIGS. 4-6 are cross-sectional views of a tip arrangement for a bottle according to a second embodiment of the present disclosure.

A second embodiment of a tip arrangement according to the present disclosure will now be described with reference to FIGS. 4-6. A bottle 200 comprises a flexible plastic resin reservoir portion 210 and a plastic top portion 220 having threads 225 and a flat top surface 220a. An overcap 230 having threads 235 to mate with the threads 225 of bottle 200 has an inner cavity 230a. A tip insert 240 mates with cavity 230a, and has an insert body 240e, a sharp piercing point 240a at its lower end for piercing the top 220a of the bottle 200, a passage 240b extending from the distal end of the sharp piercing point 240a, through insert body 240e, to an opposing upper surface of the tip insert body 240e; a precisely formed dispensing tip 240c in the upper body surface communicating with the passage 240b, and a cylindrical guide wall 240d. Guide wall 240d extends downward from the tip insert body 240e and mates with the outer wall of top portion 220 of bottle 200 to align the piercing point 240a to a predetermined position on the top surface 220a of bottle 200 prior to piercing. Dispensing tip 240c has a surface area (i.e., a width and a height) such that it forms small drops of the high-viscosity liquid to be dispensed from bottle 200.

After the piercing point 240a pierces the top surface 220a of the bottle 200, it retains the tip insert 240 on the top surface 220a of bottle 200. The piercing point 240a includes a flange 240a1 substantially parallel to the tip insert body lower surface 240e1, and a shaft 240a2 disposed between the flange 240a1 and the tip insert body lower surface 240e1. The shaft 240a2 has a length substantially the same as a thickness of the bottle top surface 220a. The bottle top surface 220a is captured between the flange 240a1 and the tip insert body lower surface 240e1 after piercing by the piercing point 240d to retain the tip insert 240 on the top surface 220a.

Figure 5:
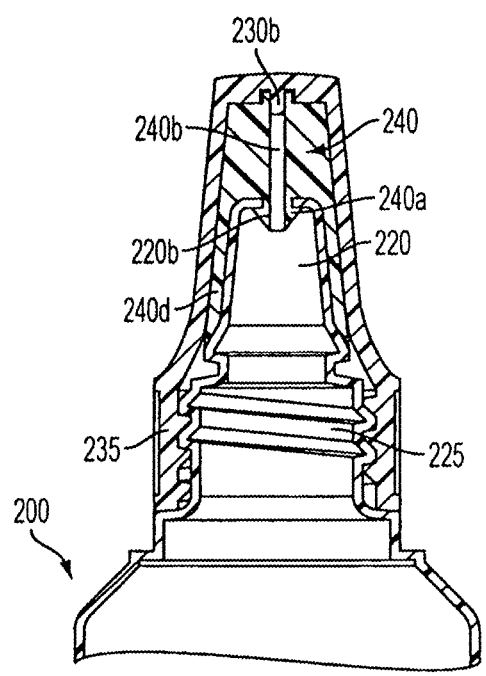
Figure 6:
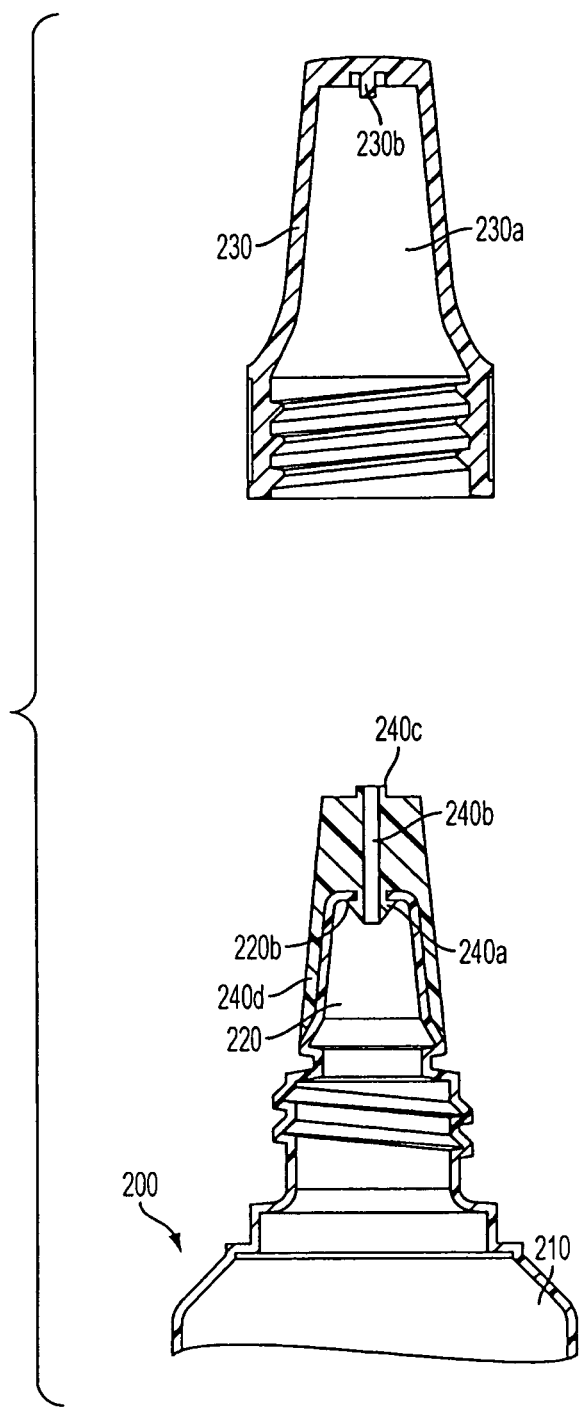
Figure 7A:
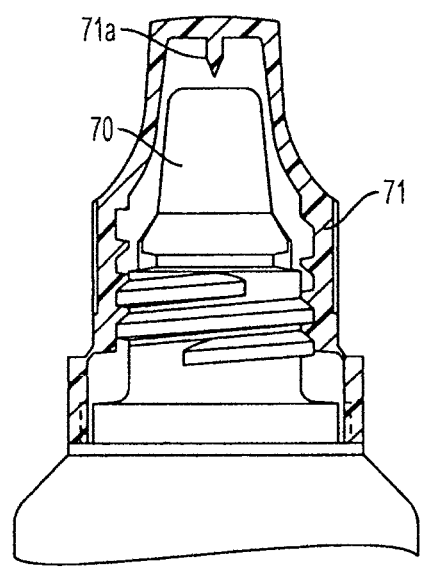
FIGS. 7a-c are cross-sectional views of a prior art tip arrangement for a bottle.
Figure 7B:
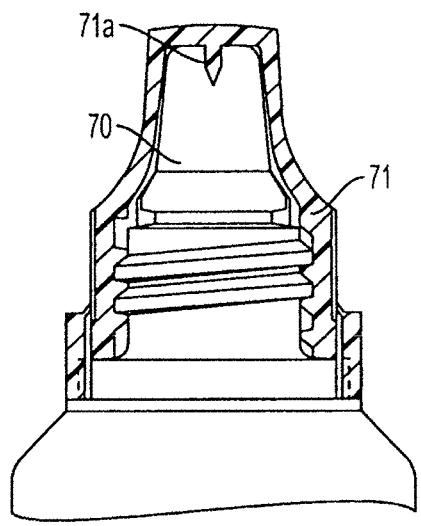
Figure 7C:
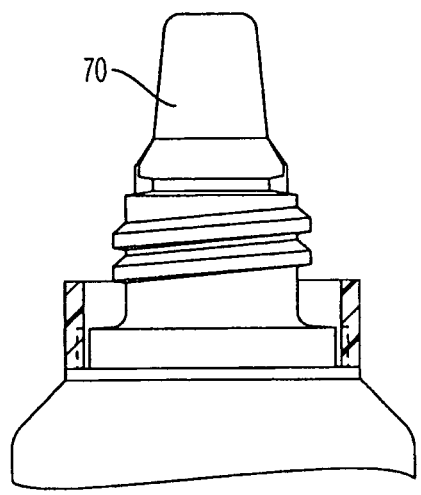

In use, the tip insert 240 is placed over the top portion 220 of bottle 200 as shown in FIG. 5, guided by the guide wall 240d to align the piercing point 240a with the top surface 220a of the bottle 200. The overcap 230 is then threaded onto bottle 200. Guide wall 240d mates with the inner surface of the overcap 230 to help guide the piercing point 240a, and the engaging sets of threads 225, 235 draw the overcap 230 down towards the bottle 200 until the piercing point 240a of the tip insert 240 is forced through the top surface 220a of the bottle to pierce it. After piercing the bottle top surface 220a, and unscrewing the threads to remove the overcap 230, the dispensing tip 240c provides the proper size orifice to dispense a liquid inside the bottle (see FIG. 6). Moreover, after the bottle top surface 220a is pierced, and the overcap 230 is threaded back onto the bottle 100 completely, an extension 230b of overcap 230 engages the orifice of the dispensing tip 240c to prevent leakage of the liquid.

In further embodiments of the present disclosure, the tip insert 240 includes threads in addition to or instead of the guide wall 240d, which mate with threads of the bottle 200 such that the top surface 220a is pierced when the tip insert is completely threaded onto bottle 200. An overcap is provided to screw or snap on to the tip insert.

The present disclosure can be practiced by employing conventional materials, methodology and equipment. Accordingly, the details of such materials, equipment and methodology are not set forth herein in detail. In the previous descriptions, numerous specific details are set forth, such as specific materials, structures, chemicals, processes, etc., in order to provide a thorough understanding of the disclosure. However, it should be recognized that the present disclosure can be practiced without resorting to the details specifically set forth. In other instances, well known processing structures have not been described in detail, in order not to unnecessarily obscure the present disclosure.

Only a few examples of the present disclosure are shown and described herein. It is to be understood that the disclosure is capable of use in various other combinations and environments and is capable of changes or modifications within the scope of the inventive concepts as expressed herein.

What is claimed is:

1. A tip insert for a dropper bottle containing a fluid, the tip insert comprising:
   an insert body presenting a surface for engaging a top surface of the bottle;
   a sharp piercing point extending from an internal surface of the insert body for piercing the top surface of the bottle;
   a flange disposed above the sharp piercing point for retaining the tip insert on the top surface of the bottle after penetration of the top surface by the sharp piercing point;
   a shaft having a length substantially the same as a thickness of the bottle top surface, the shaft being disposed between the flange and the insert body so as to render the pierced top surface of the bottle in captured engagement with the flange and the insert body after penetration of the top surface by the sharp piercing point;
   a passage extending from a distal end of the sharp piercing point, through the shaft and the insert body, to an opposing upper surface of the insert body, the sharp piercing point and the passage being dimensioned such that the sharp piercing point pierces the top surface of the bottle; and a dispensing tip at the insert body upper surface communicating with the passage for forming drops of the liquid from the bottle.

2. The tip insert of claim 1, further comprising a guide wall extending from the tip insert body for mating with an outer wall of the bottle to guide the sharp piercing point to a predetermined position on the top surface of the bottle prior to piercing the top surface of the bottle.

3. The tip insert of claim 2, wherein the guide wall is cylindrical and extends downward from the tip insert body.

4. The tip insert of claim 1, wherein the tip insert body is configured for mating with an overcap having threads for engaging corresponding threads on the bottle, to guide the sharp piercing point to a predetermined position on the top surface of the bottle prior to piercing the top surface of the bottle.

5. A dropper bottle assembly, comprising:
   a dropper bottle for containing and dispensing a liquid, the bottle having a top surface, an outer wall adjacent to the top surface, and a first set of threads;
   a tip insert comprising:
      an insert body presenting a surface for engaging the top surface of the bottle;
      a sharp piercing point extending from an internal surface of the insert body for piercing the top surface of the bottle;
      a flange disposed above the sharp piercing point for retaining the tip insert on the top surface of the bottle after penetration of the top surface by the sharp piercing point;
   a shaft having a length substantially the same as a thickness of the bottle top surface, the shaft being disposed between the flange and the insert body so as to render the pierced top surface of the bottle in captured engagement with the flange and the insert body after penetration of the top surface by the sharp piercing point;
      a passage extending from a distal end of the sharp piercing point, through the shaft and the insert body, to an opposing upper surface of the insert body, the sharp piercing point and the passage being dimensioned such that the sharp piercing point pierces the top surface of the bottle;
      a dispensing tip at the insert body upper surface communicating with the passage for forming drops of the liquid from the bottle; and
      an overcap having a second set of threads for engaging the first set of threads to draw the overcap down towards the bottle, and an inner surface for mating with the insert body to guide the sharp piercing point to a predetermined position on the top surface of the bottle prior to piercing the top surface of the bottle;
   wherein when the first and second sets of threads are engaged to draw the overcap down towards the bottle, the sharp piercing point of the tip insert pierces the top surface of the bottle.

6. The assembly of claim 5, wherein the inner surface of the overcap is configured for mating with the outer wall of the bottle to guide the sharp piercing point to the predetermined position on the top surface of the bottle.

7. The assembly of claim 5, wherein the tip insert further comprises a guide wall extending from the tip insert body configured for mating with the outer wall of the bottle to guide the sharp piercing point to a predetermined position on the top surface of the bottle prior to piercing the top surface of the bottle.

8. The assembly of claim 7, wherein the inner surface of the overcap is configured for mating with the guide wall of the tip insert to guide the sharp piercing point to the predetermined position on the top surface of the bottle.

9. The assembly of claim 5, wherein the overcap comprises an extension to engage the dispensing tip to prevent leakage of the liquid after the top surface of the bottle is pierced.

10. A method comprising:
   providing a dropper bottle for containing and dispensing a liquid, the bottle having a top surface and a first set of threads;
   providing a tip insert comprising an insert body presenting a surface for engaging the top surface of the bottle, a sharp piercing point extending from an internal surface of the insert body for piercing the top surface of the bottle, a flange disposed above the sharp piercing point for retaining the tip insert on the top surface of the bottle after penetration of the top surface by the sharp piercing point, a shaft having a length substantially the same as a thickness of the bottle top surface. the shaft being disposed between the flange and the insert body so as to render the pierced top surface of the bottle in captured engagement with the flange and the insert body after penetration of the top surface by the sharp piercing point, a passage extending from a distal end of the sharp piercing point through the shaft and the insert body to an opposing upper surface of the insert body, the sharp piercing point and the passage being dimensioned such that the sharp piercing point pierces the top surface of the bottle, and a dispensing tip at the insert body upper surface communicating with the passage for forming drops of the liquid from the bottle,
   locating the tip insert relative to the bottle such that the sharp piercing point is aligned with the top surface of the bottle; and
   forcing the sharp piercing point through the top surface of the bottle such that the pierced top surface of the bottle is in captured engagement with the flange and the insert body after penetration of the top surface by the sharp piercing point.

11. The method of claim 10, wherein the bottle has a first set of threads, further comprising:
   providing an overcap having a second set of threads for engaging the first set of threads to draw the overcap down towards the bottle; and
   after aligning the sharp piercing point of the tip insert with the top surface of the bottle, engaging the first and second sets of threads to draw the overcap down towards the bottle until the sharp piercing point pierces the top surface of the bottle.

* * * * *